US009056280B2

(12) United States Patent
Mabuchi et al.

(10) Patent No.: US 9,056,280 B2
(45) Date of Patent: *Jun. 16, 2015

(54) METHOD FOR STERILIZING BLOOD PURIFIER AND BLOOD PURIFIER PACKAGE

(75) Inventors: Kimihiro Mabuchi, Otsu (JP); Noriko Monden, Otsu (JP); Noriaki Kato, Otsu (JP); Yuuki Hatakeyama, Osaka (JP); Takashi Sunohara, Osaka (JP); Toshiaki Masuda, Osaka (JP)

(73) Assignee: Nipro Corporation, Osaka (JP)

( * ) Notice: Subject to any disclaimer, the term of this patent is extended or adjusted under 35 U.S.C. 154(b) by 40 days.

This patent is subject to a terminal disclaimer.

(21) Appl. No.: 11/577,235

(22) PCT Filed: Oct. 13, 2005

(86) PCT No.: PCT/JP2005/018862

§ 371 (c)(1),
(2), (4) Date: Dec. 12, 2007

(87) PCT Pub. No.: WO2006/041125

PCT Pub. Date: Apr. 20, 2006

(65) Prior Publication Data

US 2008/0087599 A1      Apr. 17, 2008

(30) Foreign Application Priority Data

Oct. 15, 2004   (JP) .................................. 2004-301779

(51) Int. Cl.
| | |
|---|---|
| *A61L 2/00* | (2006.01) |
| *B01D 65/02* | (2006.01) |
| *A61L 2/08* | (2006.01) |
| *B01D 67/00* | (2006.01) |
| *A61M 1/16* | (2006.01) |

(52) U.S. Cl.
CPC .............. *B01D 65/022* (2013.01); *A61L 2/087* (2013.01); *A61L 2202/22* (2013.01); *A61M 1/168* (2013.01); *B01D 67/0097* (2013.01); *B01D 2321/34* (2013.01)

(58) Field of Classification Search
USPC ............. 422/22; 210/500.21, 500.23, 500.28, 210/500.27, 500.41, 500.42, 645, 646
See application file for complete search history.

(56) References Cited

U.S. PATENT DOCUMENTS

| | | |
|---|---|---|
| 4,813,210 A | 3/1989 | Masuda et al. |
| 5,436,068 A | 7/1995 | Kobayashi et al. |
| 5,441,488 A | 8/1995 | Shimura et al. |
| 5,641,450 A | 6/1997 | Kobayashi et al. |
| 5,881,534 A | 3/1999 | Ahlqvist et al. |
| 5,889,093 A | 3/1999 | Hatakeyama et al. |
| 6,133,361 A | 10/2000 | Hatakeyama et al. |
| 6,605,218 B2 * | 8/2003 | Kozawa et al. .......... 210/500.21 |
| 6,776,912 B2 | 8/2004 | Baurmeister |
| 7,442,302 B2 | 10/2008 | Mabuchi et al. |
| 2001/0004976 A1 | 6/2001 | Kozawa et al. |
| 2002/0051730 A1* | 5/2002 | Bodnar et al. ................. 422/33 |
| 2005/0063859 A1 | 3/2005 | Masuda et al. |
| 2005/0072731 A1 | 4/2005 | Kozawa et al. |
| 2006/0205309 A1 | 9/2006 | Mabuchi et al. |
| 2007/0114167 A1 | 5/2007 | Mabuchi et al. |
| 2007/0187320 A1 | 8/2007 | Mabuchi et al. |
| 2007/0199891 A1* | 8/2007 | Mabuchi et al. ......... 210/500.23 |
| 2008/0000830 A1 | 1/2008 | Mabuchi et al. |
| 2008/0044643 A1 | 2/2008 | Yokota et al. |
| 2008/0067122 A1 | 3/2008 | Mabuchi et al. |
| 2008/0087599 A1* | 4/2008 | Mabuchi et al. ......... 210/500.23 |
| 2008/0142434 A1 | 6/2008 | Mabuchi et al. |

FOREIGN PATENT DOCUMENTS

| | | | |
|---|---|---|---|
| EP | 0 218 003 | A1 | 4/1987 |
| JP | 55-23620 | B2 | 6/1980 |
| JP | 58-134840 | A | 8/1983 |
| JP | 62-74364 | A | 4/1987 |
| JP | 62-204754 | A | 9/1987 |
| JP | 63-111878 | A | 5/1988 |
| JP | 04-300636 | A | 10/1992 |
| JP | 6-285152 | A | 10/1994 |

(Continued)

OTHER PUBLICATIONS

Translation of WO 98/058842, Hatayama et al., Dec. 1998, WIPO.*

(Continued)

*Primary Examiner* — Dirk Bass
(74) *Attorney, Agent, or Firm* — Leydig, Voit & Mayer, Ltd.

(57) ABSTRACT

The present invention provides a method for sterilizing a blood purifier, which method is effective to decrease the amounts of extracts from the blood purifier attributed to the deterioration of the selectively permeable separation membranes with time during and after exposure to a radioactive ray or an electron ray, and which method is highly reliable in safety when employed for hemocatharsis therapy. The present invention also provides a blood purifier package.

The present invention relates to a method for sterilizing a blood purifier which comprises substantially dried selectively permeable separation membranes as a main component, by way of the exposure of the same blood purifier to a radioactive ray and/or an electron ray, and this method is characterized in that the blood purifier is sealed in a packaging bag, together with an oxygen scavenger and a humectant or together with an oxygen scavenger capable of releasing a moisture, and is then sterilized in such a sealed state by the above exposure.

1 Claim, No Drawings

(56) References Cited

FOREIGN PATENT DOCUMENTS

| | | | |
|---|---|---|---|
| JP | 8-168524 A | 7/1996 | |
| JP | 10-165773 A | 6/1998 | |
| JP | 10-309427 A | 11/1998 | |
| JP | 2000-225326 A | 8/2000 | |
| JP | 2000-288085 A | 10/2000 | |
| JP | 2001-170167 A | 6/2001 | |
| JP | 2001-205057 A | 7/2001 | |
| JP | 2003-245526 A | 9/2003 | |
| JP | 2004-195380 A | 7/2004 | |
| WO | WO 95/033651 | 12/1995 | |
| WO | WO98/58842 | * 12/1998 | ............... 210/500.21 |
| WO | WO 98/58842 A1 | 12/1998 | |
| WO | WO 03/039721 A1 | 5/2003 | |

OTHER PUBLICATIONS

U.S. Appl. No. 11/721,766, filed Jan. 25, 2008.
U.S. Appl. No. 11/577,209, filed Nov. 20, 2007.
U.S. Appl. No. 11/573,339, filed Aug. 29, 2007.
U.S. Appl. No. 11/573,333, filed Aug. 29, 2007.
U.S. Appl. No. 10/582,052, filed Nov. 22, 2006.
U.S. Appl. No. 10/599,167, filed Sep. 21, 2006.
U.S. Appl. No. 10/559,544, filed Mar. 29, 2006.
U.S. Appl. No. 10/559,398, filed Dec. 5, 2005.
U.S. Appl. No. 10/947,323, filed Sep. 23, 2004.
Japanese Patent Office, International Search Report in International Patent Application No. PCT/JP2005/018861 (Jan. 17, 2006).
Japanese Patent Office, International Preliminary Report on Patentability in International Patent Application No. PCT/JP2005/018861 (Apr. 17, 2007).
Japanese Patent Office, Office Action in Japanese Patent Application No. 2004-301771 (Jul. 27, 2010).
Japanese Patent Office, International Search Report in International Patent Application No. PCT/JP2005/018862 (Jan. 24, 2006).
Japanese Patent Office, International Preliminary Report on Patentability in International Patent Application No. PCT/JP2005/018862 (Apr. 17, 2007).
European Patent Office, European Search Report in European Patent Application No. EP 045793649 (May 14, 2008).
Japanese Patent Office, International Search Report in International Patent Application No. PCT/JP2005/023337 (Jan. 17, 2006).
Japanese Patent Office, International Preliminary Report on Patentability in International Patent Application No. PCT/JP2005/023337 (Jun. 26, 2007).
European Patent Office, Extended European Search Report in European Application No. 05793644.5 (Sep. 18, 2013).
European Patent Office, Extended European Search Report in European Application No. 05820333.2 (Nov. 19, 2014).

* cited by examiner

METHOD FOR STERILIZING BLOOD PURIFIER AND BLOOD PURIFIER PACKAGE

TECHNICAL FIELD

The present invention relates to a method for sterilizing a blood purifier by way of exposure to a radioactive ray and/or an electron ray, and to a sterilized blood purifier package. Particularly, the present invention pertains to a method for sterilizing a blood purifier, which method is effective to decrease the amounts of extracts from the blood purifier attributed to the deterioration of the selectively permeable separation membranes and which method is highly reliable in safety when employed for hemocatharsis therapy, and to a blood purifier package.

BACKGROUND OF THE INVENTION

In hemocatharsis for therapy of renal failure, etc., blood purifiers such as hemodialyzers, hemofilters and hemodiafilters, which comprise dialysing membranes or ultrafilter membranes as separators, are widely used in order to remove urinal toxic substances and waste products in blood. The dialysing membranes and the ultrafilter membranes as separators are made of natural materials such as cellulose or the derivatives thereof (e.g., cellulose diacetate, cellulose triacetate, etc.) or synthetic polymers such as polyslufone, polymethyl methacrylate, polyacrylonitrile, etc. The importance of blood purifiers comprising hollow fiber type selectively permeable separation membranes as separators is very high in the field of dialyzers, in view of the advantages thereof such as the reduction of the amount of extracorporeal circulated blood, high efficiency of removing undesired substances in blood, and high productivity of manufacturing modules.

Blood purifiers are medical devices, and therefore, it is preferable to sterilize the blood purifiers in order to inhibit the proliferation of bacteria. For this sterilization, formalin, ethylene oxide gas, high-pressure steam, or exposure to radioactive rays such as a γ-ray or electron rays is employed, each of which exhibits its individual effect. Among those, the sterilization by exposure to a radioactive ray or an electronic ray is preferably employed because a subject in a package as it is can be directly subjected to a sterilization treatment, and because the sterilization effect of this method is excellent.

However, it is known that selectively permeable separation membranes for use in such a blood purifier and an adhesive, etc. for use in fixing such membranes tend to deteriorate due to the exposure to a radioactive ray or an electronic ray. Under such a circumstance, there are proposed methods for sterilizing blood purifiers while preventing the deterioration of membranes, an adhesive, etc. For example, a method of inhibiting the deterioration of hollow fiber membranes due to exposure to γ-ray by maintaining the hollow fiber membranes in a wet state (cf. Patent Literature 1). However, this method has the following problems: the weight of the blood purifier inevitably increases since it is needed to maintain the hollow fiber membranes in a wet state, which leads to disadvantages in the transport and handling thereof; or the hollow fiber membranes tend to burst or are damaged under such severely cold conditions that the water used to wet the membranes is frozen. Further, the preparation of a large amount of sterilized water is one of factors for higher cost. Furthermore, there is a possibility of proliferation of bacteria in a very short time interval between the completion of packaging and the starting of sterilization, since the hollow fiber membranes are intentionally maintained in a wet state which facilitates the proliferation of bacteria. As a result, it takes a long time in completely sterilizing the blood purifier thus manufactured, and undesirably, such a disadvantage induces a higher cost and poor safety.

To avoid the wet state of hollow fiber membranes and to inhibit the deterioration thereof due to exposure to a radioactive ray, a sterilization-protective agent such as glycerin, polyethylene glycol or the like is contained in the hollow fiber membranes, and such hollow fiber membranes in a dried state are exposed to γ-ray (cf. Patent Literature 2). However, this method suffers from the following problems because of the protective agent contained in the hollow fiber membranes: that is, it is difficult to suppress the moisture content of the hollow fiber membranes lower; the protective agent tends to deteriorate due to the exposure to γ-ray; and it is needed to remove the protective agent by washing the hollow fiber membranes before use.

There is disclosed a method of solving the above-discussed problems (cf. Patent Literature 3). According to this method, hollow fiber membranes of which the moisture content is not higher than 5% are exposed to a radioactive ray under an ambient atmosphere of not higher than 40% RH for their sterilization. This method is effective to solve the foregoing problems and to clear a criterion for the test regulated in the approval standards for manufacturing dialyzer type artificial kidney devices: that is, the UV absorbance (at a wavelength of 220 to 350 nm) of an extract from the hollow fiber membranes is lower than 0.1. However, this Patent Literature does not describe or suggest about the following problems: some influence of the ambient atmosphere (oxygen and water) around the hollow fiber membranes (or hollow fiber membrane modules) during the storage thereof acts to deteriorate (or oxidize and decompose) the materials of the hollow fiber membranes; and the UV absorbance of the extract (or the amount of an eluate) from the hollow fiber membranes tends to increase with time because of the deterioration of the materials of the hollow fiber membranes.

In the meantime, there is disclosed a method of suppressing the insoluble component of the materials of hollow fiber membranes to not higher than 10 wt. % by exposing the hollow fiber membranes to γ-ray with their moisture content maintained at not higher than 10 wt. % (cf. Patent Literature 4). It is described in this Patent Literature that the amount of a hydrophilic polymer which is extracted from membranes using a 40% aqueous ethanol solution is not larger than 2.0 $mg/m^2$ per one $m^2$ of the area of a surface of the membrane on its side in contact with a treated fluid.

The present inventors have intensively studied in order to improve the above-described sterilization method by way of exposure to a radioactive ray or an electron ray. As a result, they have found that the sterilization method by way of exposure to a radioactive ray or an electron ray induces the formation of hydrogen peroxide which can not be detected by the above conventional UV absorption spectrometry. As a result of this finding, it is found that a hydrophilic polymer is extracted by the above extraction method. While the mechanism of forming hydrogen peroxide is unknown, the following can be supposed: the deterioration of the base materials of selectively permeable separation membranes is induced in the presence of hydrogen peroxide; hydrogen peroixe has an influence on the increase of the amount of an eluate from the membranes, which is detected by the above UV absorbance and which tends to increase with time after the exposure to the radioactive ray or the electron ray; and the amount of hydrogen peroxide itself tends to increase with time, which further accelerates the deterioration of the materials to thereby increase the amounts of the known extracts from the membranes. Accordingly, it is known that strict control is needed for the exposure of hollow fiber membranes to the radioactive ray or the electron ray and for the following storage of the hollow fiber membranes in order to ensure safety as a blood purifier.

In the meantime, Patent Literature 3 and Patent Literature 4 do not refer to the formation of hydrogen peroxide during the storage of hollow fiber membranes and hollow fiber membrane modules, or to an absorbance (or an eluate) which tends to increase with time after the exposure to γ-ray, or to an increase in amount of a hydrophilic polymer (polyvinyl pyrrolidone) in an extract from the membranes using a 40% aqueous ethanol solution. Patent Literature 4 does not refer to the influence of a humidity of an ambient atmosphere around the hollow fiber membranes, on the deterioration of the materials of the hollow fiber membranes.

To prevent the deterioration of the base materials of medical devices attributed to the presence of oxygen, it is known that the medical devices are sealed in packaging media made of oxygen impermeable materials, together with oxygen scavengers, and are then exposed to radioactive rays, and it is also disclosed that this method can be applied to blood purifiers (cf. Patent Literature 5, Patent Literature 6 and Patent Literature 7).

The deterioration of hollow fiber membranes because of the above radiation exposure in the presence of the oxygen scavenger is accompanied by odors (described in Patent Literature 5), a decrease in strength or dialyzing performance of the base materials (described in Patent Literature 6) or a decrease in strength of the base materials or formation of aldyhydes (described in Patent Literature 7). However, any of these Patent Literatures does not refer to increases in amounts of the above extracts. Further, any of these Patent Literatures refers to the oxygen concentration in the package under the radiation exposure, but not to the importance of the moisture content of the selectively permeable separation membranes and the humidity of the ambient atmosphere.

Further, it is described that a material for the packaging bag for use in the method of sterilizing the blood purifier by way of radiation exposure in a system using the above oxygen scavenger is important to have a gas-, particularly oxygen-impermeability. However, this Literature does not refer to a moisture permeability.

Patent Literatures 8 and 9 disclose hollow fiber membrane modules which can show decreased amounts of hydrophilic polymers and which use no filling fluid, by displacing the internal atmospheres of the hollow fiber membrane modules with inert gases. However, the oxygen concentrations in the atmospheres for the sterilization of the hollow fiber membrane modules are high, and therefore, it is impossible to completely inhibit the deterioration and decomposition of the materials of the hollow fiber membranes under the radiation exposures. Consequently, the amounts of eluates from the hollow fiber membrane modules can not be reduced, and there arises a further problem that the biocompatibility of the membranes becomes poor since the materials of the membranes are crosslinked by the radiation exposures.

Patent Literature 10 discloses a technique of sealing a fluid separation membrane module in a packaging bag. According to this Patent Literature, the fluid separation membrane module and the packaging bag are filled with deairing water before the storage of the fluid separation membrane module packed in the packaging bag, and the packaging bag is made of a material capable of shutting out an air so as to seal the membrane module. This technique is intended to prevent the fluid separation membranes from partially drying due to the gasification of the air which is caused by a change in the temperature of the atmosphere during the storage of the fluid separation membranes. However, in this technique, no attention is paid to an increase in transport cost attributed to the increased weight of the package or to the proliferation of bacteria during the storage of the membranes.

Patent Literature 1: JP-B-55-23620
Patent Literature 2: JP-A-8-168524
Patent Literature 3: JP-A-2000-288085
Patent Literature 4: JP-A-2001-205057
Patent Literature 5: JP-A-62-74364
Patent Literature 6: JP-A-62-204754
Patent Literature 7: WO98/58842
Patent Literature 8: JP-A-2001-170167
Patent Literature 9: JP-A-2003-245526
Patent Literature 10: JP-A-2004-195380

DISCLOSURE OF THE INVENTION

Problems to be Solved by the Invention

Objects of the present invention are to provide a method for sterilizing a blood purifier, which method is effective to decrease the amounts of extracts from the blood purifier attributed to the deterioration of the selectively permeable separation membranes and which method is highly reliable in safety when employed for hemocatharsis therapy, and to provide a blood purifier package.

Means for Solving the Problems

The present invention relates to a method for sterilizing a blood purifier which comprises substantially dried selectively permeable separation membranes as a main component, by exposing such a purifier to a radioactive ray and/or an electron ray, and this method is characterized in that the blood purifier is sealed in a packaging bag, together with an oxygen scavenger and a humectant or together with an oxygen scavenger capable of releasing a moisture, and is then sterilized in such a sealed state.

The present invention also relates to a blood purifier package which is obtained by packing, in a packaging material, a blood purifier which comprises substantially dried selectively permeable separation membranes as a main component and which is sealed in a packaging bag, together with an oxygen scavenger and a humectant or together with an oxygen scavenger capable of releasing a moisture and is then sterilized in such a sealed state by way of exposure to a radioactive ray and/or an electron ray.

Modes for Carrying out the Invention

The selectively permeable separation membranes to be used in the present invention are substantially in a dried state. The wording of "substantially in a dried state" means that the selectively permeable separation membranes are dried sufficiently not to permit the proliferation of bacteria and not to foam a resin for use in assembling a module. The moisture content of the selectively permeable separation membranes is preferably not higher than 2.5 mass %, more preferably not higher than 2.0 mass %, still more preferably not higher than 1.5 mass %, far more preferably not higher than 1.0 mass %. When the moisture content of the selectively permeable separation membranes is too high, there are likely to arise similar disadvantages which the known methods for sterilizing separation membranes in wet states have suffered from: that is, the weight of the blood purifier increases; bacteria tend to proliferate, and so on. There are also likely to arise further problems: that is, a reaction between an urethane resin and water is likely to cause a failure in adhesion of a bundle of hollow fiber membranes with an urethane-based resin adhesive or the like for fixing the bundle in a housing to assemble a module; or an eluate from the membranes tends to increase in amount because of the formation of side products due to the reaction of the adhesive with water. The lower the moisture content of the selectively permeable separation membranes, the better it is, because there is less possibility to cause the above-described problems. However, too low a moisture content of the membranes is likely to increase the amount of the eluate from the blood purifier, although why such an event occurs is not well known. Accordingly, the moisture content of the membranes is preferably not lower than 0.5 mass %, more preferably not lower than 0.7 mass %, still more preferably not lower than 1.0 mass %, far more preferably not lower than 1.25 mass %.

In the present invention, the moisture content (mass %) of the hollow fiber membrane can be easily calculated by the following equation:

Moisture content (mass %)=$(a-b)/a \times 100$ wherein (a) represents the mass of the hollow fiber membrane before drying, and (b) represents the mass of the bone-dried hollow fiber membrane after drying in an oven at 120° C. for 2 hours.

Herein, by adjusting the mass (a) of the hollow fiber membrane to from 1 to 2 g, the hollow fiber membrane can be bone-dried (i.e. a dried state in which the hollow fiber membrane shows no further change in mass) in 2 hours.

Preferably, the selectively permeable separation membranes to be used in the present invention comprise a hydrophobic polymer containing a hydrophilic polymer. As raw materials for the hydrophobic polymer to be used in the present invention, there are preferably used cellulose-based polymers such as regenerated cellulose, cellulose acetate and cellulose triacetate, polysulfone-based polymers such as polysulfone and polyethersulfone, polyaclyronitrile, polymethyl methacrylate, ethylene-vinyl alcohol copolymers, and the like. Among them, cellulose-based polymers and polysulfone-based polymers are preferable, because the use of them facilitates the manufacturing of selectively permeable separation membranes having high water permeability. Cellulose diacetate and cellulose triacetate are preferable among the cellulose-based polymers, because the use of them makes it easy to reduce the thickness of such membranes. The polysulfone-based polymers represent a generic name of resins having sulfone bonds, and preferable examples thereof include, but not limited to, polysulfone resins and polyethersulfone resins having repeating units of the following formulas, which are commercially available with ease:

[Chemical formula 1]

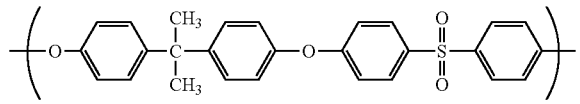

[Chemical formula 2]

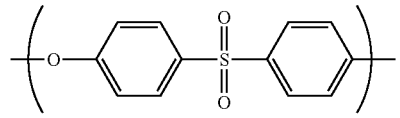

Examples of the hydrophilic polymer to be used in the present invention include materials such as polyethylene glycol, polyvinyl alcohol, carboxylmethyl cellulose, polyvinyl pyrrolidone and the like, which form micro phase separation structures with the hydrophobic polymers in solutions. In view of safety and cost, the use of polyvinyl pyrrolidone is preferred. Specifically, it is preferable to use polyvinyl pyrrolidone having a molecular weight of 9,000 (K17), which is commercially available from BASF. Likewise, it is preferable to use polyvinyl pyrrolidones having molecular weights of 45,000 (K30), 450,000 (K60), 900,000 (K80) and 1,200,000 (K90), each of which may be used alone or in combination according to an end use and in order to obtain intended properties and structure. It is more preferable to use polyvinyl pyrrolidone having a molecular weight of 450,000 to 1,200,000, since polyvinyl pyrrolidone having a higher molecular weight is hard to be eluted.

The radioactive ray or the electro ray to be used in the present invention is α-ray, β-ray, γ-ray, electron ray or the like. In view of sterilization efficiency and handling ease, γ-ray or an electron ray is preferably employed. While not limited, the dose of a radioactive ray or an electron ray is such a dose as to ensure the sterilization of the blood purifier. In general, the dose thereof is preferably from 10 to 30 kGy.

In the present invention, the blood purifier comprising substantially dried selectively permeable separation membranes as a main component is sealed in a packaging bag, together with an oxygen scavenger and a humectant or together with an oxygen scavenger capable of releasing a moisture, and is then exposed in such a sealed state to a radioactive ray and/or an electron ray for the sterilization thereof. This method is effective to inhibit the deterioration of the base materials of the selectively permeable separation membranes, attributed to the exposure to the radioactive ray or the electron ray for the sterilization, and is also effective to suppress increases in the amounts of deteriorated substances determined by UV absorbance, the hydrophilic polymer extracted with an aqueous ethanol solution and extracted hydrogen peroxide. Furthermore, there can be obtained an unexpected effect that increases in the amounts of the above extracted substances with time after the sterilization can be suppressed. Accordingly, the reliability in safety of the blood purifier when used for hemocatharsis is markedly improved.

A preferable oxygen scavenger to be used in the present invention has a function to release a moisture, in addition to an oxygen-scavenging function. Examples of an agent capable of scavenging an oxygen include as a general-purpose oxygen scavenger, sulfite, hydrogensulfite, dithionite, hydroquinone, catechol, resorcinol, pyrogallol, gallic acid, rongalite, ascorbic acid and/or a salt thereof, sorbose, glucose, lignin, dibutylhydroxytoluene, dibutylhydroxyanisole, ferrous salt, metal powder (e.g. and iron powder, etc.) and the like. The oxygen scavenger may be appropriately selected from these materials for use. An oxygen scavenger mainly comprising metal powder, if needed, may contain, as an oxidation catalyst, one or more compounds selected from halogenated metal compounds such as sodium chloride, potassium chloride, magnesium chloride, calcium chloride, aluminum chloride, ferrous chloride, ferric chloride, sodium bromide, potassium bromide, magnesium bromide, calcium bromide, iron bromide, nickel bromide, sodium iodide, potassium iodide, magnesium iodide, calcium iodide, iron iodide, etc. To impart a moisture-releasing function, a moisture release type oxygen scavenger (for example, Ageless® Z-200PT manufactured by Mitsubishi Gas Chemical Company, Inc.), or a humectant such as a porous carrier (e.g. zeolite powder impregnated with a water content) is packed together with the blood purifier. Further, other functional fillers such as a deodorant may be included in the packaging bag. The form of the oxygen scavenger is not limited, and it may be in the form of powder, particles, mass or sheet; or it may be a sheet- or film-shaped oxygen scavenger obtained by dispersing an oxygen absorber composition in a thermoplastic resin.

As the selectively permeable separation membranes of the present invention, flat membranes, hollow fiber membranes and the like can be used. Among them, the hollow fiber membranes are preferable, because the membrane area per volume can be increased, so that a compact module having a high dialyzing efficiency can be obtained by using such hollow fiber membranes.

The selectively permeable separation membranes and the blood purifier of the present invention can be manufactured by known processes. For example, the hollow fiber type selectively permeable separation membranes are manufactured by extruding a membrane-forming dope from the sheath portion of a double hollow spinneret and extruding an internal injection solution which keeps the hollow portions of the membranes, from the core portion of the spinneret, followed by immersing the semi-solid membrane fibers in a solidifying fluid. Preferably, the hollow fiber membranes manufactured by any of these methods should have inner diameters of 150 to 300 μm and thickness of 10 to 70 μm.

For example, the blood purifier of the present invention is manufactured by inserting a bundle of the above hollow fiber membranes into a housing for the blood purifier, pouring a potting agent such as polyurethane in both ends of the membrane bundle to thereby seal both ends thereof, cutting off an excess of the potting agent from both ends thereof to open the end faces of the hollow fiber membranes, and attaching a header to the housing.

The effect of the present invention can be exhibited by appropriately controlling the humidity of the inner atmosphere around the selectively permeable separation membranes incorporated into the blood purifier, by making use of the moisture-releasing function of the oxygen scavenger or the humectant which is one of the constituents of the present invention. In a preferred mode of the present invention, the relative humidity in the inner atmosphere of a sealed packaging bag at a room temperature is not lower than 50% RH, more preferably not lower than 55% RH, still more preferably not lower than 60% RH, far more preferably not lower than 65% RH. When the relative humidity is lower than 50% RH, the selectively permeable separation membranes are gradually dried while the blood purifier is being stored, which is likely to increase the amount of an eluate therefrom. Particularly when the moisture content of the hydrophilic polymer decreases, the wettability of the separation membranes tends to lower when the membranes are again wetted, or elution is likely to occur from the membranes. Accordingly, it is preferable to select an oxygen scavenger having such a moisture-releasing function that can achieve the above-specified humidity in the inner atmosphere of the packaging bag. When the use of only the oxygen scavenger is insufficient to achieve the above-specified humidity because of the weak moisture-releasing function of the oxygen scavenger, a humectant is used together with such an oxygen scavenger to compensate for the insufficient humidity. This method is also included in the scope of the present invention. A higher humidity in the inner atmosphere of the packaging bag is preferable, because the decomposition and deterioration of the hydrophilic polymer can be inhibited, and because the storage stability for the blood purifier is improved. However, too high a relative humidity permits dewing in the packaging bag, which is likely to lower the quality of the blood purifier. Accordingly, the relative humidity is more preferably not higher than 95% RH, still more preferably not higher than 90% RH.

In the present invention, the foregoing effects can be exhibited by controlling the relative humidity of the inner atmosphere of the packaging bag, on the prerequisite that the relative humidity around the selectively permeable separation membranes within the blood purifier is maintained within the above specified range. Accordingly, in the blood purifier within the packaging bag, it is preferable to communicate the included selectively permeable separation membranes with an external from the housing within the packaging bag. In other words, it is preferable to open the inlet and outlet of the passage for the blood and the inlet and outlet of the passage for a dialysing fluid, of the blood purifier.

In the present invention, the relative humidity is calculated from a partial vapor pressure (p) and a saturated vapor pressure (P) at room temperatures, by the equation: Relative Humidity (%)=p/P×100. This measurement is conducted as follows: the sensor probe of a temperature- and humidity-measuring instrument (ONDOTORI RH Type manufactured by T&D) is inserted into a packaging bag, and then, the bag is sealed to continuously measure the relative humidity within the bag.

Another effect of the oxygen scavenger of the present invention is its own individual oxygen-scavenging effect. That is, the oxygen concentration of the inner atmosphere of the packaging bag is decreased, as the oxygen scavenger absorbs the oxygen in the packaging bag, so that the oxidation and deterioration of the materials of the selectively permeable separation membranes, the adhesive and the casing, constituting the blood purifier, can be inhibited while the blood purifier is being sterilized by exposure to a radioactive ray or an electron ray, and while such a blood purifier is being stored before and after the sterilization, and so that increases in the amounts of the substances extracted from the blood purifier can be suppressed. Therefore, preferably, the blood purifier should be exposed to a radioactive ray or an electron ray under the condition where the oxygen concentration of the inner atmosphere of the packaging bag has been sufficiently decreased. Thus, the oxygen concentration is preferably lower than 5%, more preferably lower than 3%, still more preferably lower than 1%, far more preferably lower than 0.5%, particularly lower than 0.1%. For example, when the gas in the inner atmosphere of the bag is an air, the oxygen concentration of the inner atmosphere of the bag usually decreases to 0.1% or lower after 48 hours or so has passed since the blood purifier was sealed in the packaging bag. Accordingly, preferably, it is 2 days after the sealing of the bag that the blood purifier in the packaging bag should be exposed to a radioactive ray or an electron ray. In this regard, too long a time interval between the sealing of the bag and the sterilization of the blood purifier is likely to permit the proliferation of bacteria, and thus, the sterilization of the blood purifier should be done within 10 days, preferably 7 days, more preferably 5 days after the sealing of the bag.

Preferably, the packaging bag to be used in the present invention is made of an oxygen- and water vapor-impermeable material, since the use of such a material is effective to maintain the humidity and the oxygen concentration of the sealed atmosphere within the above-specified ranges over a long period of time to thereby inhibit the deterioration of the components of the blood purifier with time before and after the exposure and to thereby inhibit increases in the amounts of the extracts from the blood purifier. Accordingly, the oxygen permeability of the packaging bag is preferably at most 1 $cm^3/(m^2 \cdot 24 \text{ hr.atm})$ (20° C., 90% RH). When the oxygen permeability is too high, the oxygen-absorbing capacity of the oxygen scavenger saturates during a long period of storage, and the materials of the membrane, particularly the hydrophilic polymer in the membrane, are gradually oxidized and decomposed to thereby increase the amounts of eluates from the membrane. Thus, the oxygen permeability of the packaging bag is more preferably at most 0.8 cm$^3$/(m$^2$.24 hr.atm) (20° C., 90% RH), still more preferably at most 0.6 cm$^3$/(m$^2$.24 hr.atm) (20° C., 90% RH).

The water vapor permeability of the packaging bag is preferably at most 5 g/(m$^2$.24 hr.atm) (40° C., 90% RH). When the water vapor permeability of the packaging bag is too high, the membranes are likely to be too dried or humidified depending on the storage conditions, which may increase the amounts of eluates from the blood purifier. Thus, the water vapor permeability of the packaging bag is more preferably at most 4 g/(m$^2$.24 hr.atm) (40° C., 90% RH), still more preferably at most 3 g/(m$^2$.24 hr.atm) (40° C., 90% RH).

The materials and structure of the packaging bag to be used in the present invention may be optionally selected, so long as the above properties are satisfied. Preferable examples of the material for the packaging bag are oxygen- and water vapor-impermeable materials such as an aluminum foil, aluminum-deposited film, inorganic oxide-deposited film of silica and/or alumina, vinylidene chloride type polymer composite film and the like. The sealing method for the packaging bag also may be optionally selected. For example, the packaging bag may be sealed by any of the heat sealing method, impulse heat sealing method, fusion sealing method, frame sealing method, ultrasonic sealing method, high frequency sealing method and the like. Thus, the material for the packaging bag is preferably a composite material of a film having a sealing property and any of the above impermeable materials. Particularly preferable is a laminate sheet comprising a structural layer of an aluminum foil capable of substantially shutting out an oxygen gas and a water vapor, an outer layer of a polyester film, an intermediate layer of an aluminum foil, and an inner layer of a polyethylene film, since this laminate sheet has both of impermeability and a heat sealing property.

Preferably, the blood purifier of the present invention should meet the following amounts of extracts therefrom when used for hemodialysis.

(1) The UV absorbance of an extract at 220 to 350 nm according to the approved standards for manufacturing dialyzer type artificial kidney devices is lower than 0.10.

(2) The amount of a hydrophilic polymer extracted from the blood purifier, using a 40% aqueous ethanol solution is not larger than 2.0 mg/m$^2$ per 1.0 m$^2$ of a surface of the membrane on its treated fluid-contacting side.

In the known technologies, keen attentions have been paid to the amounts of the extracts (1) and (2) as the values found just after the sterilizing treatment, however, quite no attention is paid to increases in the amounts of the above extracts with time after the sterilizing treatment. The reliability in safety as a blood purifier can be markedly improved by the present invention which is accomplished by introducing the elucidation of these novel events.

EXAMPLES

Hereinafter, the effects of the present invention will be described by Examples thereof, which, however, should not be construed as limiting the scope of the present invention in any way. The physical properties of the following Examples are evaluated as follows. In Examples, the abbreviation "ND" means "not detected".

1. Calculation of Area of Membranes

The area of membranes in a dialyzer was calculated by the following equation, based on the inner diameter of the hollow fiber membrane:

$$A(m^2) = n \times \pi \times d \times L$$

In the equation, n represents the number of hollow fiber membranes in the dialyzer; π represents the ratio of the circumference of a circle to its diameter; d represents the inner diameter (m) of the hollow fiber membrane; and L represents the effective length (m) of the hollow fiber membranes in the dialyzer.

2. UV Absorbance (at 220 to 350 nm) According to Approved Standards for Manufacturing Dialyzer Type Artificial Kidney Devices Extraction and measurement were conducted according to the methods regulated in the approved standards for manufacturing dialyzer type artificial kidney devices. A sample of hollow fiber membranes (1 g) was admixed with pure water (100 mg), and the mixture was subjected to extraction at 70° C. for one hour to prepare a test solution. Then, the UV absorbance of this test solution at a wavelength of 220 to 350 nm was measured. According to the above standard, the maximum absorbance is regulated to lower than 0.1.

3. Amount of Hydrophilic Polymer Extracted with 40% Aqueous Ethanol Solution

A case of polyvinyl pyrrolidone (PVP) as an example of hydrophilic polymers is described.

A module with its passage on the dialysing fluid side closed was connected to a silicone tube circuit, and pure water was allowed to pass through the passage on the blood side of the module to fill both the module and the circuit with pure water. After that, a 40 v/v % ethanol solution was allowed to pass through the passage on the blood side of the module at a flow rate of 150 ml/min., and 100 ml of the same solution was discharged from the outlet of the circuit. The inlet and the outlet of the passage on the blood side were closed with forceps, and the passage on the dialyzing fluid side was successively filled with the 40 v/v % ethanol solution, and was again closed. The 40 v/v ethanol solution, the circuit and the module were all controlled to 40° C., and the ethanol solution was circulated at a flow rate of 150 ml/min. Sixty minutes after, all the fluids in the circuit and the module were discharged and collected together with the circulating fluid to measure the volume of the mixture. The fluid on the dialysing fluid side was separately collected to measure its volume. The PVP contents of the respective fluids were measured according to the following procedure. A sample of each fluid (2.5 ml) was admixed with 0.2 mol/L citric acid (1.25 ml), and the mixture was stirred. Then, 0.006N iodine (500 µL) was added, and the resulting mixture was stirred and was left to stand at a room temperature for 10 minutes. After that, the absorbance of the resultant solution was measured. When the PVP content of the solution was high, the solution was diluted to be 10 or 100 times larger in volume, and then, the PVP content of the resulting solution was measured. The PVP content in the sample was calculated from an analytical curve prepared under the same conditions, to thereby calculate the amount of eluted PVP (mg/m$^2$) per module (1.0 m$^2$).

4. Oxygen Concentration in Packaging Bag

The measurement was conducted by gas chromatography, using a column filled with a molecular sieve (13X-S mesh 60/80 manufactured by GL Science), an argon gas as a carrier gas, and a detector of heat-conduction system. An analysis was made at a column temperature of 60° C. A gas within a packaging bag was collected by directly pricking the closed packaging bag with a syringe needle.

5. Oxygen Permeability of Packaging Material

An oxygen permeability-measuring apparatus (OX-TORAN 100 manufactured by Modern Controls) was used to measure the oxygen permeability of the material of a packaging bag at 20° C. and 90% RH.

6. Water Vapor Permeability of Packaging Material

A water vapor permeability-measuring apparatus (PARMATRAN-W manufactured by Modern Controls) was used to measure the water vapor permeability of the material of the packaging bag at 40° C. and 90% RH.

7. Moisture Content of Hollow Fiber Membrane

To find a moisture content (mass %) of a hollow fiber membrane, the mass (a) of the hollow fiber membrane before dried and the mass (b) of the same hollow fiber membrane after dried at 120° C. in an oven for 2 hours (bone-dried) were measured. The moisture content was calculated by the following equation:

Moisture content (mass %)=(a−b)/a×100 wherein, if the mass (a) of the hollow fiber membrane is from 1 to 2 g, the hollow fiber membrane could be bone-dried in 2 hours (if bone-dried, the membrane shows no further change in mass).

Example 1

A spinning dope was prepared from polyethersulfone (4800P, manufactured by Sumika Chem Tex Co., Ltd.) (18.6 mass %), polyvinyl pyrrolidone (Kollidon K90 manufactured by BASF) (3.4 mass %) as a hydrophilicity-imparting agent, water (2.0 mass %) as a non-solvent, triethylene glycol (TEG manufactured by MITSUI CHEMICALS, INC.) (30.4 mass %) and dimethylacetamide (DMAc) (manufactured by Mitsubishi Gas Chemical Corporation) (45.6 mass %). The spinning dope was extruded from the outer slit of a double spinneret maintained at 45° C., and water as an inner solution was extruded from the inner injection hole of the double spinneret. The resulting semi-solid hollow fiber was allowed to pass through an air gap with a length of 600 mm at a spinning rate of 60 m/minute, and was then dipped in a solidifying bath of 70° C. (DMAc:TEG:water=12:8:90). After that, the hollow fiber was washed with pure water of 45° C. for one minute followed by pure water of 80° C. for 90 seconds, and then was wound onto a hank. Thus, the hollow fiber membrane with an inner diameter of 199.5 μm and a thickness of 29.5 μm was obtained.

About 10,100 hollow fiber membranes thus obtained were inserted into a polyethylene pipe, which was then cut with a predetermined length. After that, the hollow fiber membranes in the pipe were dried in a hot air drier at 40° C. until the moisture content in the hollow fiber membranes became 0.6 mass %. Thus, a bundle of the hollow fiber membranes was obtained.

The bundle was inserted into a casing, and the end portions of the bundle were bonded with an urethane resin. After that, the end portions of the bundle were cut out. Thus, a blood purifier of which the selectively permeable separation membranes were opened at their both ends was made up. This blood purifier was sealed in a packaging bag together with two moisture-release type oxygen scavengers (Ageless Z-200PT manufactured by Mitsubishi Gas Chemical Company, Inc.). In this regard, the packaging bag was made of an aluminum lamination sheet which had an outer layer of a polyester film, an intermediate layer of an aluminum foil and an inner layer of a polyethylene film and which had an oxygen permeability of at most 0.5 cm$^3$/(m$^2$.24 hr.atm) and a water vapor permeability of at most 0.5 g/(m$^2$.24 hr.atm). After the sealing, the packed blood purifier was stored at a room temperature. The humidity and the oxygen concentration in the inner atmosphere of the packaging bag, the moisture content of the selectively permeable separation membranes, and the UV absorbance of an eluate and the amount of an extract from ethanol in an elution test were measured and determined after 1 day, 1 month and 3 months have passed after the sealing, respectively. The results are shown in Tables 1 and 2.

Comparative Example 1

A blood purifier was made up of the same selectively permeable separation membranes as those used in Example 1, in the same manner as in Example 1. A blood purifier package was obtained in the same manner as in Example 1, except that the blood purifier was packed in a packaging bag, together with two general-purpose type oxygen scavengers (TAMOTSU® manufactured by OJITAC). The resultant blood purifier package was stored in the same manner as in Example 1. The results of the evaluation of the selectively permeable separation membranes which changed in properties with time are shown in Tables 1 and 2. It was supposed that the amount of an eluate increased since the entanglement of the hydrophilic polymer and the hydrophobic polymer became weak because of too small a moisture content in the packaging bag.

Comparative Example 2

A bundle of selectively permeable separation membranes was obtained in the same manner as in Example 1, except that the moisture content of the selectively permeable separation membranes, found immediately after the drying, was changed to 8.8 mass % by lowering the drying degree of the same membranes.

While a blood purifier was made up in the same manner as in Example 1, a failure in the adhesion of the membranes occurred because of the foaming of the urethane resin. This foaming was supposed to occur because of the reaction between the urethane resin and the moisture in the selectively permeable separation membranes.

Comparative Example 3

A blood purifier package was obtained in the same manner as in Example 1, except that no oxygen scavenger was used, and the resultant blood purifier package was stored in the same manner as in Example 1. The results of the evaluation of the blood purifier which changed in properties with time are shown in Tables 1 and 2. It was supposed that the amount of an eluate from the blood purifier increased with time since the oxidation and decomposition of the hydrophilic polymer proceeded because of the influence of the oxygen in the system.

Example 2

A blood purifier package was obtained in the same manners as in Example 1, except that the blood purifier was sealed in a packaging bag, together with the same general-purpose oxygen scavenger as that used in Comparative Example 1, and a humectant which was prepared by sealing zeolite powder having adsorbed water (zeolite (10 g)+water content (10 g)) in a perforation type moisture permeable packing material (having a water vapor permeability of 500 g/(m$^2$.24 hr.atm) (40° C., 90% RH). The resultant blood purifier package was stored in the same manner as in Example 1. The results of the evaluation of the blood purifier which changed in properties with time are shown in Tables 1 and 2.

Example 3

A blood purifier package of Example 2 was obtained in the same manners as in Example 1, except that an electron ray exposure apparatus with an acceleration voltage of 5,000 KV was used instead of the γ-ray. The results of the evaluation of the blood purifier which changed in properties with time are shown in Tables 1 and 2.

TABLE 1

|  | Just after sterilization | | | 1 month after sterilization | | | 3 months after sterilization | | |
| --- | --- | --- | --- | --- | --- | --- | --- | --- | --- |
|  | Moisture content (mass %) | Relative humidity (% RH) | Oxygen concentration (%) | Moisture content (mass %) | Relative humidity (% RH) | Oxygen concentration (%) | Moisture content (mass %) | Relative humidity (% RH) | Oxygen concentration (%) |
| Ex. 1 | 0.6 | 72 | ND | 0.9 | 71 | ND | 2.1 | 72 | ND |
| Ex. 2 | 0.6 | 68 | ND | 1.0 | 70 | ND | 2.2 | 68 | ND |
| Ex. 3 | 0.6 | 72 | ND | 0.8 | 71 | ND | 1.8 | 72 | ND |
| C. Ex. 1 | 0.5 | 21 | ND | 0.5 | 20 | ND | 0.5 | 20 | ND |
| C. Ex. 2 | — | — | — | — | — | — | — | — | — |
| C. Ex. 3 | 0.6 | 71 | 25 | 2.1 | 70 | 26 | 2.0 | 70 | 27 |

TABLE 2

|  | Just after sterilization | | 1 month after sterilization | | 3 months after sterilization | |
| --- | --- | --- | --- | --- | --- | --- |
|  | UV absorbance | Extract from ethanol (mg/m²) | UV absorbance | Extract from ethanol (mg/m²) | UV absorbance | Extract from ethanol (mg/m²) |
| Ex. 1 | 0.03 | 1.3 | 0.04 | 1.3 | 0.04 | 1.4 |
| Ex. 2 | 0.05 | 1.4 | 0.04 | 1.4 | 0.04 | 1.4 |
| Ex. 3 | 0.03 | 1.3 | 0.05 | 1.6 | 0.05 | 1.6 |
| C. Ex. 1 | 0.07 | 1.8 | 0.18 | 2.7 | 0.22 | 3.1 |
| C. Ex. 2 | — | — | — | — | — | — |
| C. Ex. 3 | 0.05 | 1.3 | 0.23 | 3.2 | 0.36 | 4.3 |

INDUSTRIAL APPLICABILITY

The blood purifier, sterilized by exposure to a radioactive ray and/or an electron ray according to the sterilization method of the present invention, is markedly improved on its reliability in safety when used for hemocatharsis, because there can be inhibited the formation of various extracts from the blood purifier, attributed to the deterioration of the components of the blood purifier, particularly to the deterioration of the selectively permeable separation membranes with time during and after the above exposure. Therefore, the present invention will significantly contribute to this industry.

The invention claimed is:

1. A method for sterilizing a blood purifier, which method comprises
    (a) providing a blood purifier comprising substantially dried selectively permeable separation membranes as a main component, wherein the selectively permeable separation membrane comprises a polysulfone-based polymer containing polyvinyl pyrrolidone, and wherein the moisture content of the selectively permeable separation membrane is not lower than 0.5 mass % and not higher than 2.2 mass %,
    (b) packing and sealing the blood purifier in a packaging bag, together with (i) an oxygen scavenger and a humectant or (ii) an oxygen scavenger capable of releasing moisture, under conditions that provide an atmosphere of a relative humidity of not less than 68% RH at room temperature in the sealed packaging bag, wherein the water vapor permeability of the sealed packaging bag is not higher than 5 g/(m².24 hr.atm) (40° C. and 90% RH), and the oxygen permeability of the sealed packaging bag is not higher than 1 cm³/(m².24 hr.atm) (20° C. and 90% RH), and
    (c) exposing the packed and sealed blood purifier to a radioactive ray and/or an electron ray, so as to sterilize the blood purifier.

* * * * *